(12) United States Patent
Madson (10) Patent No.: US 9,557,335 B2
(45) Date of Patent: Jan. 31, 2017

(54) METHOD OF ISOLATING AND IDENTIFYING FRUIT OLIGOSACCHARIDES FROM RIPE BANANA FRUIT

(71) Applicant: BIOLOGISTICS LLC, Ames, IA (US)

(72) Inventor: Michael A Madson, Ames, IA (US)

(73) Assignee: BIOLOGISTICS LLC, Ames, IA (US)

( * ) Notice: Subject to any disclaimer, the term of this patent is extended or adjusted under 35 U.S.C. 154(b) by 0 days.

(21) Appl. No.: 14/792,951

(22) Filed: Jul. 7, 2015

(65) Prior Publication Data

US 2015/0323540 A1 Nov. 12, 2015

Related U.S. Application Data

(63) Continuation-in-part of application No. 14/534,546, filed on Nov. 6, 2014, which is a continuation-in-part of application No. 13/426,891, filed on Mar. 22, 2012, now Pat. No. 8,993,226.

(60) Provisional application No. 61/513,921, filed on Aug. 1, 2011.

(51) Int. Cl.
| | |
|---|---|
| *C12Q 1/00* | (2006.01) |
| *G01N 13/00* | (2006.01) |
| *G01N 30/84* | (2006.01) |
| *G01N 33/20* | (2006.01) |
| *G01N 37/00* | (2006.01) |
| *G01N 33/58* | (2006.01) |
| *G01N 33/548* | (2006.01) |

(52) U.S. Cl.
CPC ............ *G01N 33/58* (2013.01); *G01N 33/548* (2013.01)

(58) Field of Classification Search
None
See application file for complete search history.

(56) References Cited

U.S. PATENT DOCUMENTS

| | | | | |
|---|---|---|---|---|
| 3,911,145 A * | 10/1975 | Marion | ............... | A23F 3/405 426/386 |
| 5,859,333 A * | 1/1999 | Keeling | ............... | A01H 5/10 435/101 |
| 5,972,344 A * | 10/1999 | Edwards | ............... | A23L 1/2215 424/59 |
| 2004/0062882 A1 * | 4/2004 | Liebmann-Vinson | | C12N 5/0068 428/34.1 |
| 2010/0068806 A1 * | 3/2010 | Laine | .................. | C12N 5/0606 435/366 |
| 2011/0159121 A1 * | 6/2011 | McDaniel | ............... | A61K 8/97 424/727 |

OTHER PUBLICATIONS

Der Agopian et al. J. Agric. Food Chem. 2008, 56, 3305-3310.*
Chandraju et al. J. Chem. Pharm. Res., 2011, 3(3):312-321.*
Wichienchot et al. (Songklanakarin J. Sci. Technol. 33 (5), 517-523, Sep.-Oct. 2011.*
Der Agopia R.G. et al., "Synthesis of fructooligosaccharides in banana 'prata' and its relation to Invertase activity and sucrose accumulation", J. Agric. and Food Chem. 57 (22):10765-71, (2009).
Bacon, J.S.D., "The trisaccharide fraction of some monocotylendons", Biochem J. (1959) 73 (3) 507-514.
Bacon, J.S.D. et al., "The carbohydrates of Jerusalem artichoke heart and other compositae", Biochem. J. (1951) 48 (1) 114-126.
Forsythe, K.L. et al., "The detection of isokestose and neokestose in plant extracts by CNMR" Carbohydr. Res. 185:315-319 (1989).
Forsythe, K.L. et al., "Detection of kestoses and neokestose-related oligosaccharides in extracts of Fatsuca arundinacea, Dactylls glomerata and Asparagus officinatis cultures and Invertase C and H nuclear magnetic resonance spectroscopy" Plant Physiol. 92 1014-1020 (1990).
Fuller, K.W. et al., "A micromethod for the separation and determination of polysaccharides by zone electrophoresis", Biochem. J. (1956) 64 (4) 657-663.
Killian, S. et al., "The effect of novel bifidogenic trisaccharide, neokestose, on the human colonic microbiota", World J. of Microbiology and Biotechnology (2002) 18(7) 637-644.
Shiomi, N., "Isolation and identification of 1-kestodse and neokestose from onion bulbs J. of the Faculty of Agriculture—Hokkaido University" (1978) 58(4) 548-556.
Suzuki, T. et al., "Confirmation of fructose biosynthesized from [1-13C] glucose in asparagus tissue using MALDI-TOF-MS and ESI-MS" J. Plant Physiol. 170 (8) 715-22 (2013).

* cited by examiner

*Primary Examiner* — Chris R Tate
*Assistant Examiner* — Douglas F White
(74) *Attorney, Agent, or Firm* — Zarley Law Firm, P.L.C.

(57) ABSTRACT

A laboratory method used for isolating and identifying fruit oligosaccharides from ripe banana fruit is provided. The method includes the step of obtaining a predetermined amount of a plant, such as banana fruit and combining it with ethanol. The method also includes the step of isolating an oligosaccharide from the plant without adding heat to the ethanol. The method can be used to isolate and identify neokestose-1,6-diphosphate.

8 Claims, 9 Drawing Sheets

METHOD OF ISOLATING AND IDENTIFYING FRUIT OLIGOSACCHARIDES FROM RIPE BANANA FRUIT

CROSS REFERENCE TO A RELATED APPLICATION

This application is a continuation in part of U.S. application Ser. No. 14/534,546, filed Nov. 6, 2014, which is a continuation in part of U.S. application Ser. No. 13/426,891, filed Mar. 22, 2012, which claims the benefit of U.S. Provisional Application No. 61/513,921, filed Aug. 1, 2011.

BACKGROUND OF THE INVENTION

This invention relates to a method of testing for a fruit oligosaccharide. More specifically, this invention relates to a method of isolating and identifying fruit oligosaccharides in banana fruit.

Kestoses are fructosyl sucrose derivatives that are found in many plants, including bananas. In *Biochem J.* 48(1) 114-126 (1951), Bacon and Eldeman found bananas contain neokestose and 6-kestose, which are trisaccharides, and bifrucose, which is a tetraose. The isolation and identification of these oligosaccharides are important as they hold a potential key to the treatment of various diseases.

Fruit oligosaccharides have been found to inhibit glycolysis, which is used by various life-threatening diseases. For instance, cancer cells have a high glycolytic rate when compared to healthy tissue. By inhibiting glycolysis, fruit oligosaccharides can be used to treat cancer patients.

Fruit oligosaccharides can also act as an inhibitor in the treatment of other diseases. The inhibition of glycolytic aldolase A and C has been shown to assist in preventing neurodegenerative diseases, such as amyotropic lateral schlerosis (ALS) and Alzheimers Disease. Aldolase inhibition may also be a key to treatment of tuberculosis by stifling the metabolism of Mycobacterium tuberculosi.

Various methods of isolation and identification have been used in the past. Using an acetate conversion, fruit oligosaccharides have been analyzed using carbon-13 nuclear magnetic resonance (CNMR) to determine the isomeric kestoses in plants by Forythe et al. in *Plant Physiol.* 92(4) 1014-1020 (1990) and Forsythe and Feather in *Carbohydr. Res.* 185 315-319 (1989). 2D-NMR has also been used by Lieu et al. in *Carbohydr. Res.* 18; 217 43-49 (1991) to make chemical shift assignment to 6-kestose and neokestose. Matrix-assisted laser desorption/ionization coupled with time of flight mass spectrometry (MALDI-TOF MS) and electrospray ionization mass spectrometry (ESI-MS) have been used by Sukzuki et al. in *Plant Physiol.* 170(8) 715-722 (2013) to confirm the presence of fructans in plant tissue, such as asparagus tissue. Other methods, such as zone electrophoresis used by Fuller et al. *Biochem. J.* 64(4) 657-663 (1956), paper chromatography, celite column chromatography, silica gel chromatography, and thin layer chromatography (TLC), have been used to separate and identify molecules.

Despite these advances in plant oligosaccharide isolation and identification, problems remain. Specifically, none of these methods have allowed for the isolation and structural characterization of phosphorylated or di-phosphorylated kestoses in plants. For instance, Agopia et al. *n J. Agric. And Food Chem.* 57(22) 10765-10771 (2009), claimed to confirm the presence of nekestose, 6-kestose, and bifurcose in banana 'prata,' but was unable to report any phosphorylated or di-phosphorylated kestoses.

Additionally, researchers, such as Shiomi in *J. of the Faculty of Agriculture-Hokkaido University* 54(4) 548-556 (1978), have used ethanol in a boiling water bath to complete extraction. Others, like Bacon and Edelman in *Biochem J.* 48(1) 114-126 (1951), have heated the mixtures to 80° C. for a period of 10 to 15 minutes to allow extraction. The heating of ethanol is time consuming, dangerous, destructive, and inefficient.

Thus, it is a primary objective of the invention to provide a method for isolating a fruit oligosaccharide in order to determine the oligosaccharide's disease-treatment capabilities.

Another objective of the invention is to provide a method for identifying a fruit oligosaccharide in order to determine the oligosaccharide's disease-treatment capabilities.

Yet another objective of the invention is to provide a method for characterizing phosphorylated and di-phosphorylated kestoses.

Another objective of the invention is to provide a hydride addition reaction for discernment of phosphate/sulfate ester substitution.

Yet another objective of the invention is to provide a method of extraction that does not use heat.

Another objective of the invention is to provide a method of extraction that has increased efficiency.

Yet another objective of the invention is to provide a method of extraction that is not unnecessarily degenerative.

These and other objectives, features, and advantages of the invention will become apparent from the specification and claims.

SUMMARY OF THE INVENTION

A laboratory method used for isolating and identifying fruit oligosaccharides from ripe banana fruit is provided. The method includes the step of obtaining a predetermined amount of a plant, such as banana fruit, and combining it with ethanol. The method also includes the step of isolating an oligosaccharide from the plant without adding heat to the ethanol. The method can be used to isolate and identify neokestose-1,6-diphosphate.

DETAILED DESCRIPTION

The figures show a system 10 utilized to isolate and identify a fruit oligosaccharide from a banana. The system 10 includes a centrifuge tube 12 such as an Eppendorf tube, a centrifuge 14, a test tube 16, such as an Eppendorf tube, and an analytical instrument 18.

The system 10 also includes a plant, such as a fruit, or banana fruit 20, ethanol 22, ammonia ($NH_3$) aqueous solution 24, and sodium borohydride ($NaBH_4$) 26. In an exemplary embodiment, 95% ethanol 20, 1M ammonia aqueous solution 24, and 4M sodium borohydride 26 in dimethyl ethyl ether triethylene glycol solution is used. Other embodiments that vary the concentration of these solutions is also contemplated.

Ethanol Extraction

Figure 1:
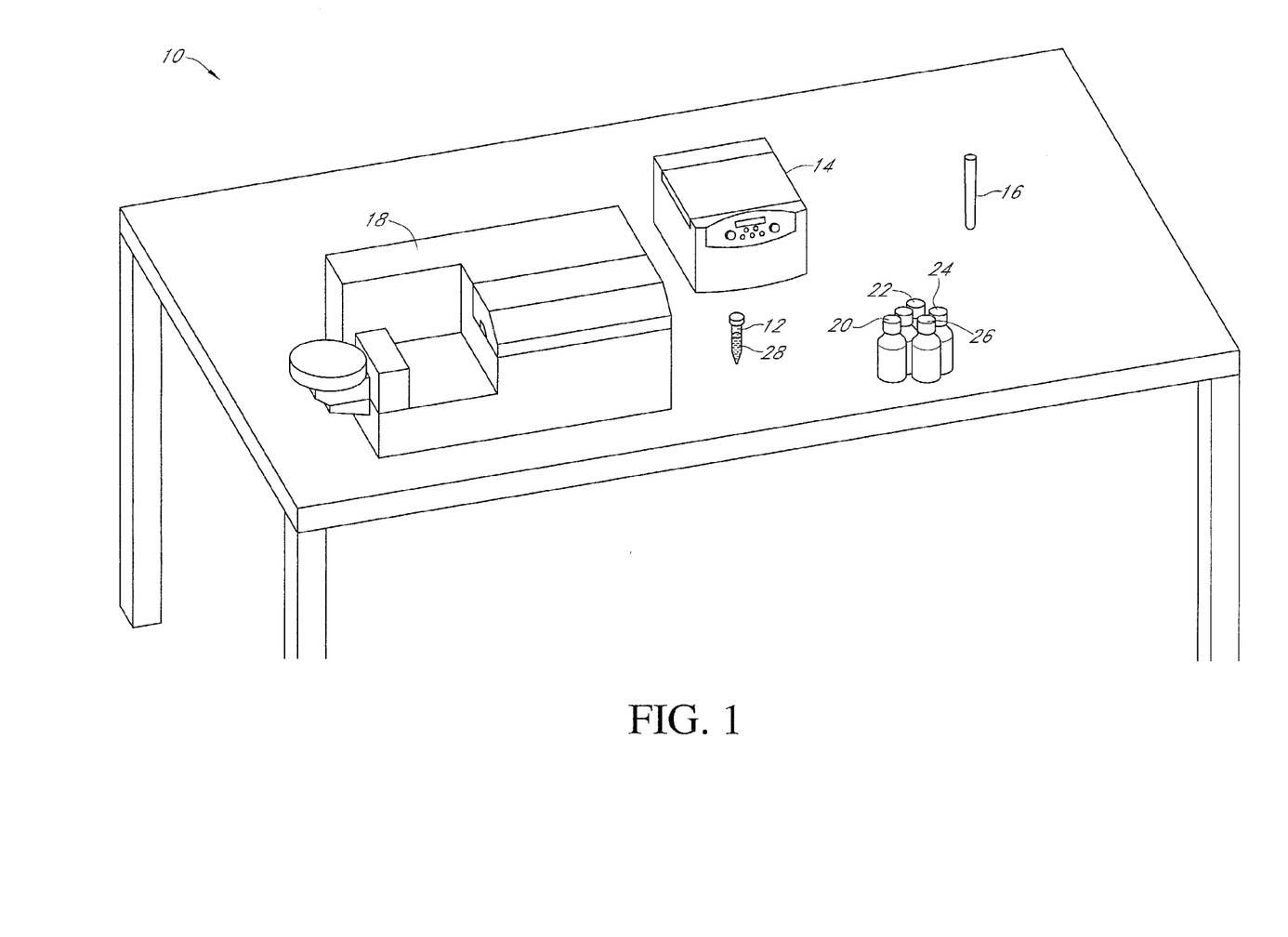
FIG. 1 is a perspective view of the system of isolating and identifying fruit oligosaccharides from banana fruit.
Figure 2:
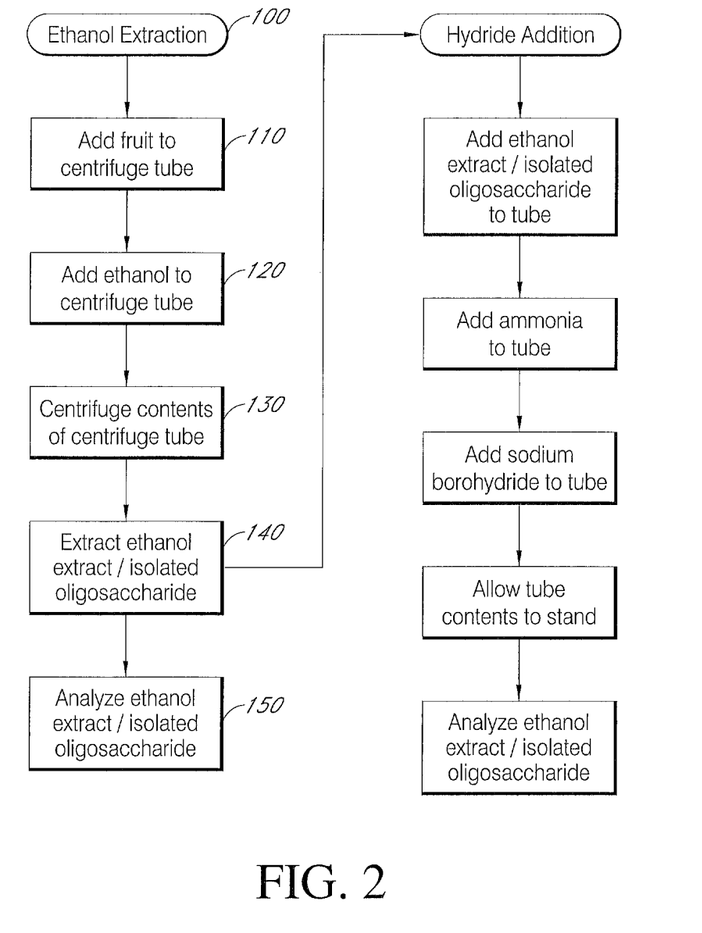
FIG. 2 is a is a diagram of the method of isolating and identifying fruit oligosaccharides from banana fruit.

The ethanol extraction 100 begins at step 110 by adding a predetermined amount of banana fruit 20 to the centrifuge tube 12. In one embodiment, 40 mg of banana fruit 20 is added to the centrifuge tube 12.

At step 120 a predetermined amount of ethanol 22 is added to the centrifuge tube 20 that contains the banana fruit 20. In an exemplary embodiment the ethanol 20 is 1.0 mL of 95% ethanol 22. Other volumes and masses are contemplated, and, in particular amounts, those amounts that maintain the ratio between banana fruit 20 and ethanol 22 described.

The use of 95% ethanol 22 eliminates the need to heat the ethanol 22. Because no heat is added, the concentration of the resulting ethanol extract or isolated oligosaccharide 28 is lower, which prevents the pH of the ethanol extract 28 from dropping. If heated, the lowered pH of the ethanol extract 28 would create acidic conditions that could hydrolyze any phosphates present and degrade any present sugars.

The centrifuge tube 12 is closed and placed in the centrifuge 14 at step 130 and centrifuged for a predetermined amount of time. In one embodiment, the centrifuge 14 is ran for 20 seconds at 14,600×g. At step 140 the ethanol extract 28 is removed from the centrifuge tube 12 and let to stand at ambient temperatures for a predetermined amount of time. In an exemplary embodiment, the ethanol extract 28 is let stand less than 3 weeks.

After being left to stand, the ethanol extract 28 is analyzed using the analytical instrument 18 at step 150. For example, the ethanol extract 28 can be analyzed using inductively coupled plasma electrospray ionization mass spectrometry (ICP ESI-MS) or with tandem mass spectrometry (MS/MS) in a negative ion mode. Analysis under these conditions, however, is incapable of discerning between phosphate esters and sulfate esters as they are isobaric.

Hydride Addition

To discern between whether the ions produced by the analytical instrument are phosphorylated or sulfated, a hydrate addition method 200 is used. Beginning at step 210, ethanol extract 28 placed in the test tube 16 at a predetermined amount. In an illustrative embodiment, 200 μL of ethanol extract 28 are placed in a 1.5 mL Eppendorf tube 16. At step 220, a predetermined amount of ammonia 24, for example 1.0 mL of 1M ammonia, is added to the tube 16. Next, at step 230, a predetermined amount of sodium borohydride 26 solution is added to the tube 16. In one embodiment, 3 μL of sodium borohydride 26 solution is added. Other volumes are hereby contemplated and particularly those that maintain the ratio of solutions just set forth.

The contents of the tube 16 are allowed to stand for a predetermined amount of time at step 240. In an exemplary embodiment, the contents are allowed to stand for less than three weeks.

Analysis is conducted at step 250 using the analytical device 28. For instance, analysis can be done with an ICP ESI-MS and MS/MS. The hydride addition 200 allows for discernment in phosphorylation versus sulfation based on sulfated molecules having a slightly higher amu of approximately 1 amu for a dianionic compound and 2 amu for a monoanionic ion from the ESI-TOF MS.

Using the above ethanol extraction 100 and hydride addition 200, a fruit oligosaccharide can be identified and characterized.

Identification

Figure 3:
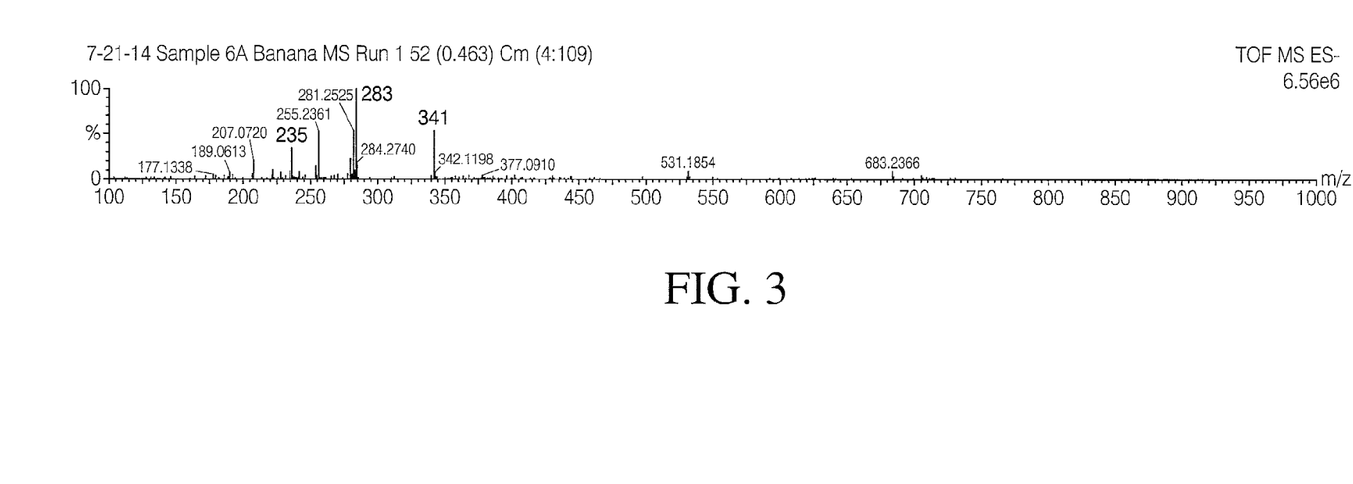
FIG. 3 is a mass spectrum obtained using the method of isolating and identifying fruit oligosaccharides.
Figure 4:
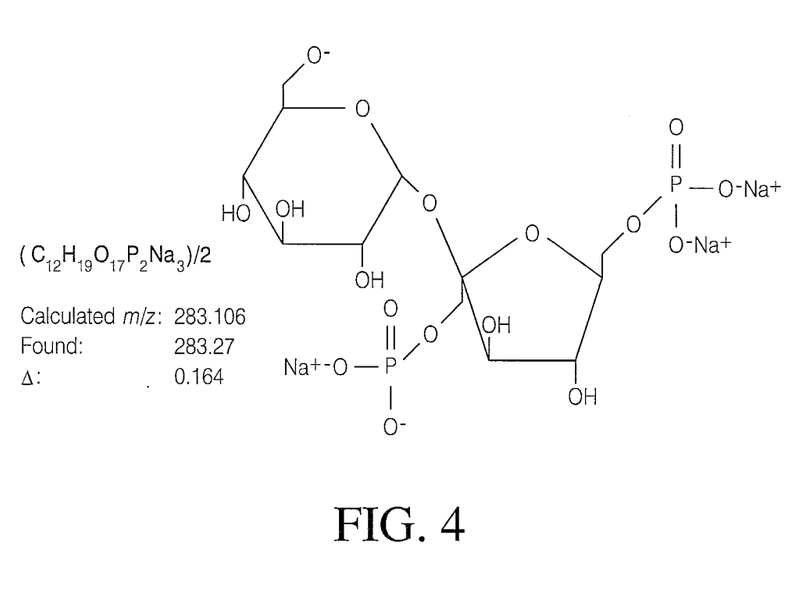
FIG. 4 is a diagram of an ion identified using the method of isolating and identifying fruit oligosaccharides from banana fruit.
Figure 5:
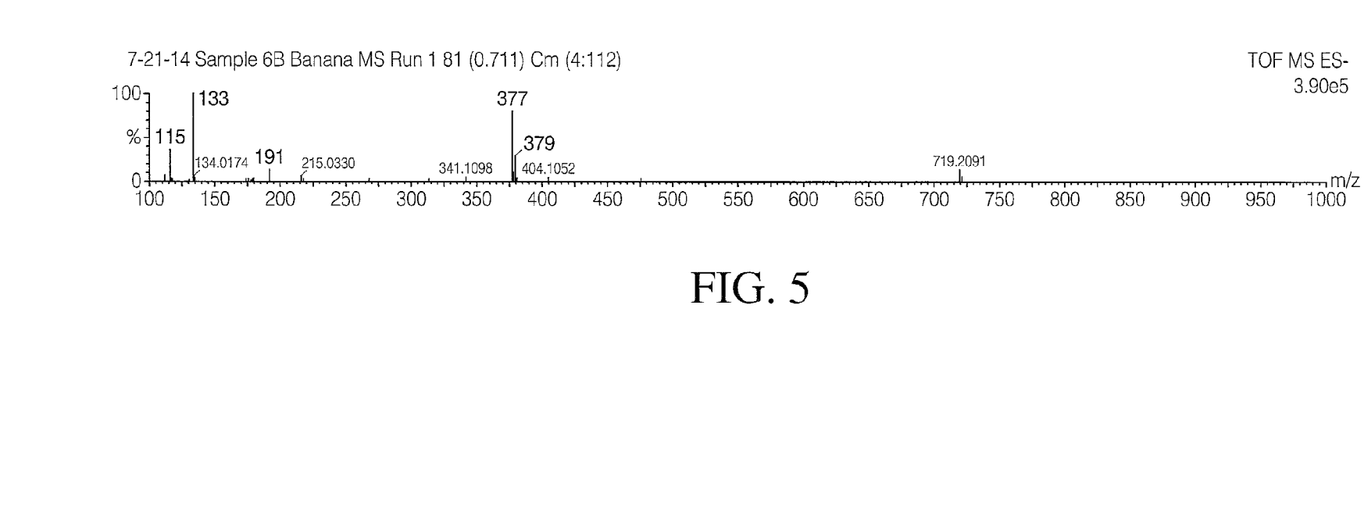
FIG. 5 is a is a mass spectrum obtained using the method of isolating and identifying fruit oligosaccharides.
Figure 6:
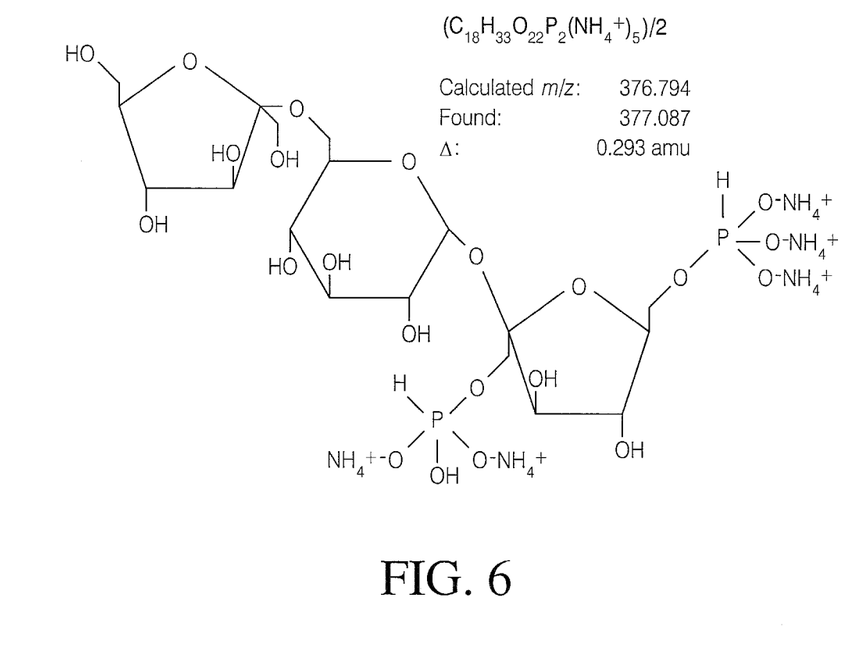
FIG. 6 is a diagram of an ion identified using the method of isolating and identifying fruit oligosaccharides from banana fruit.
Figure 7:
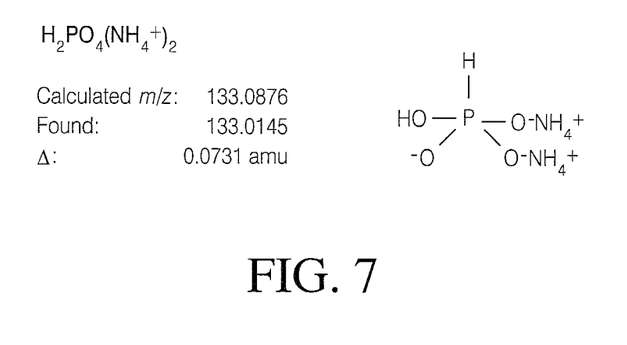
FIG. 7 is a diagram of an ion identified using the method of isolating and identifying fruit oligosaccharides from banana fruit.

By way of example, neokestose-1,6-diphosphate was identified using the above-described method. As seen in FIG. 3, the negative ion ESI-MS of the ethanol extract 28 shows a base peak at m/z 283. The structure of the peak at m/z 283 is shown in FIG. 4, which shows a cleavage product anion that is consistent with neokestose-1,6-diphosphate. FIG. 5 shows the mass spectrum of a hydride derivatized neokestose derivative using hydride addition 200 to discern between sulfate and phosphate identity with a peak at 377 m/z. FIG. 6 shows the fully derivatized structure of the trisaccharide, which is consistent with neokestose di-(monohydrido)-phosphate for the peak at 377 m/z. FIG. 7 shows an anion that supports that the phosphate ester is mono-hydride substituted and cleaved.

Figure 8:
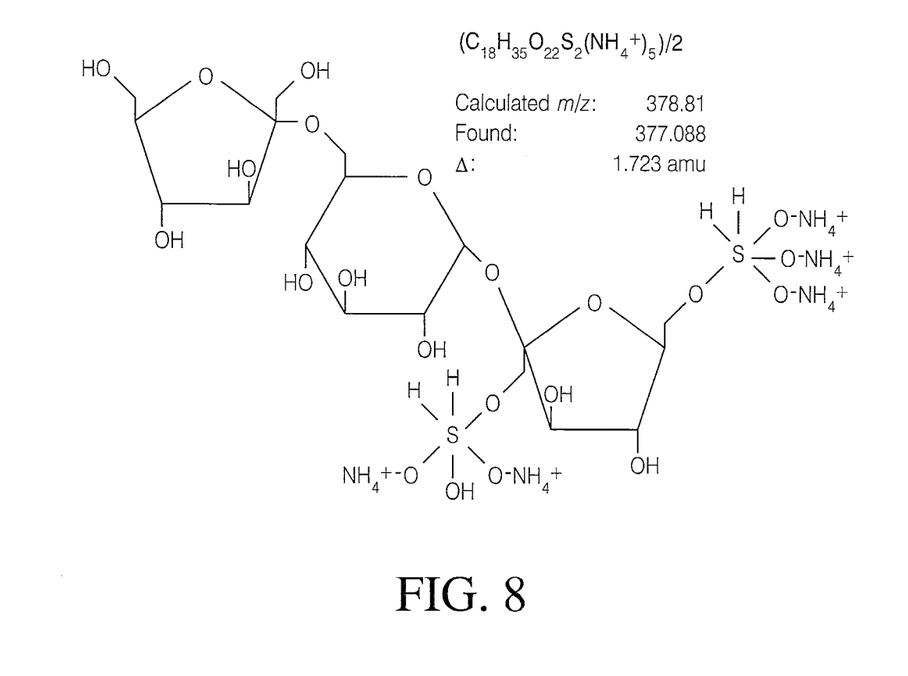
FIG. 8 is a diagram of an ion identified using the method of isolating and identifying fruit oligosaccharides from banana fruit.
Figure 9:
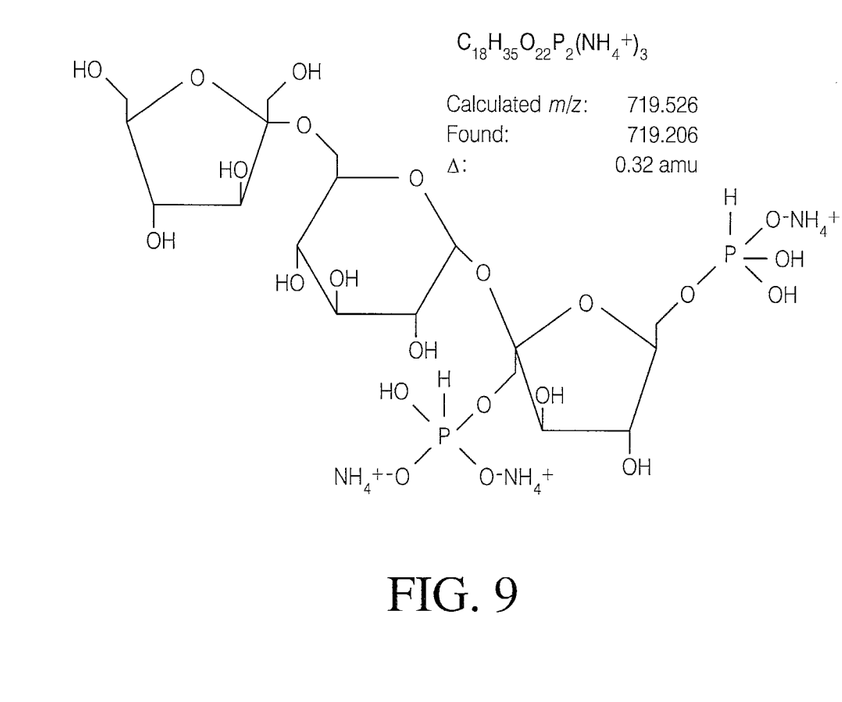
FIG. 9 is a diagram of an ion identified using the method of isolating and identifying fruit oligosaccharides from banana fruit.

FIG. 8 shows how the hydride addition 200 is used to discern between a sulfated and phosphorylated neokestose-1,6-di ester. The figure shows the di-(dihydrido)sulfate analogue of neokestose-1,6-disulfate along with the calculated and found molecular mass, which is beyond the accuracy of the mass spectrometer 18, indicating the molecule is neokestose-1,6-diphosphate. FIG. 9 shows an ionized neokestose-1,6-diphosphate. FIGS. 3-9 demonstrate the identification of a fruit oligosaccharide, in this example neokestose-1,6-diphosphate, using the described method.

Therefore, a method of isolating and identifying fruit oligosaccharides from ripe banana fruit has been provided that allows for the identification and isolation of oligosaccharides to determine disease-treatment capability, discernment of phosphate/sulfate substitution, does not use heat, has increased efficiency, avoids unnecessary degeneration, and improves upon the art.

From the above discussion and accompanying figures and claims it will be appreciated that the method of isolating and identifying fruit oligosaccharides from ripe banana fruit offers many advantages over the prior art. It will also be appreciated by those skilled in the art that other modifications could be made without parting from the spirit and scope of the invention and fall within the scope of the claims and are intended to be covered thereby.

What is claimed is:

1. A method of isolating, identifying, and characterizing fruit oligosaccharides comprising the steps of:
   obtaining a predetermined amount of a banana fruit;
   combining the predetermined amount of the banana fruit with ethanol to form an ethanol extract solution;
   centrifuging the ethanol extract solution for a predetermined amount of time;

allowing the ethanol extract solution to stand at ambient temperatures for a predetermined amount of time;

isolating an oligosaccharide from the banana fruit without adding heat to the ethanol;

characterizing the isolated oligosaccharide by hydride addition to form a hydride addition solution;

allowing the hydride addition solution to stand at ambient temperature for a predetermined amount of time;

analyzing the hydride addition solution with an analysis device; and identifying a residual oligosaccharide in the hydride addition solution.

2. The method of claim 1 further comprising the step of analyzing the oligosaccharide for the presence of phosphorylated and sulfated esters.

3. The method of claim 1 further comprising the step of adding a predetermined amount of ammonia and sodium borohydride to the isolated oligosaccharide.

4. The method of claim 1 wherein the plant is ripe banana fruit.

5. The method of claim 1 further comprising the step of identifying the isolated oligosaccharide as neokestose-1,6-diphosphate.

6. The method of claim 1 wherein the ethanol is 95% ethanol.

7. The method of claim 1 wherein the ethanol and the banana fruit are combined in a ratio of 40 mg of banana fruit to 1.0 mL of ethanol.

8. The method of claim 1 wherein the ethanol extract solution stands for no less than three weeks.

* * * * *